United States Patent
Nakaya et al.

(10) Patent No.: US 11,832,990 B2
(45) Date of Patent: Dec. 5, 2023

(54) ULTRASONIC DIAGNOSTIC APPARATUS, AND MEDICAL DATA PROCESSING APPARATUS

(71) Applicant: CANON MEDICAL SYSTEMS CORPORATION, Otawara (JP)

(72) Inventors: Shigemitsu Nakaya, Nasushiobara (JP); Jiro Higuchi, Otawara (JP); Yutaka Kobayashi, Nasushiobara (JP); Atsushi Nakai, Nasushiobara (JP); Kazuo Tezuka, Nasushiobara (JP); Yoshitaka Mine, Nasushiobara (JP); Shunsuke Satoh, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 503 days.

(21) Appl. No.: 16/390,076

(22) Filed: Apr. 22, 2019

(65) Prior Publication Data
US 2019/0328358 A1 Oct. 31, 2019

(30) Foreign Application Priority Data

Apr. 26, 2018 (JP) ................................. 2018-085036
Apr. 15, 2019 (JP) ................................. 2019-076786

(51) Int. Cl.
*A61B 8/00* (2006.01)
*A61B 8/14* (2006.01)
(Continued)

(52) U.S. Cl.
CPC ........ *A61B 8/4427* (2013.01); *A61B 5/02055* (2013.01); *A61B 8/06* (2013.01);
(Continued)

(58) Field of Classification Search
CPC ......... A61B 5/02055; A61B 8/06; A61B 8/14; A61B 8/4416; A61B 8/4427; A61B 8/463;
(Continued)

(56) References Cited

U.S. PATENT DOCUMENTS 9,355,309 B2   5/2016   Tridandapani et al.
2009/0099449 A1*  4/2009   Lundberg ............ G01S 7/52074
                                                        600/443
(Continued)

FOREIGN PATENT DOCUMENTS

CN   102727248 A   10/2012
JP   2010-136873 A   6/2010
(Continued)

OTHER PUBLICATIONS

Office Action dated Oct. 4, 2022, in corresponding Japanese Patent Application No. 2019-076786, 7 pages.

*Primary Examiner* — Yi-Shan Yang
*Assistant Examiner* — Alexei Bykhovski
(74) *Attorney, Agent, or Firm* — Oblon, McClelland, Maier & Neustadt, L.L.P.

(57) ABSTRACT

The ultrasonic diagnostic apparatus according to a present embodiment includes processing circuitry. The processing circuitry is configured to: acquire at least one of optical image data and sound data as data related to a confirmation item corresponding to a disorder name of a subject or an examination type for an ultrasonic scan; associate the ultrasonic image data acquired by the ultrasonic scan with the data related to the confirmation item; and store the association in a memory.

14 Claims, 10 Drawing Sheets

(51) Int. Cl.
 A61B 8/08 (2006.01)
 A61B 5/0205 (2006.01)
 A61B 8/06 (2006.01)
(52) U.S. Cl.
 CPC ................ *A61B 8/14* (2013.01); *A61B 8/488* (2013.01); *A61B 8/5207* (2013.01); *A61B 8/5292* (2013.01); *A61B 8/463* (2013.01); *A61B 8/483* (2013.01)
(58) Field of Classification Search
 CPC ....... A61B 8/483; A61B 8/488; A61B 8/5207; A61B 8/5292
 See application file for complete search history.

(56) References Cited

U.S. PATENT DOCUMENTS

| | | |
|---|---|---|
| 2014/0024939 A1 | 1/2014 | Kato et al. |
| 2014/0205165 A1 | 7/2014 | Jeanne et al. |
| 2015/0048956 A1 | 2/2015 | Chapusot |
| 2017/0000462 A1* | 1/2017 | Washburn ............ A61B 8/5215 |
| 2017/0100098 A1* | 4/2017 | Urabe .................... A61B 8/468 |
| 2017/0367651 A1* | 12/2017 | Tzvieli ................. A61B 5/0816 |
| 2018/0353160 A1 | 12/2018 | Oura et al. |
| 2019/0008450 A1* | 1/2019 | Gurievsky ........... A61B 5/4812 |
| 2019/0076127 A1* | 3/2019 | Aase ...................... A61B 8/463 |

FOREIGN PATENT DOCUMENTS

| | | |
|---|---|---|
| JP | 2011-005025 | 1/2011 |
| JP | 5134721 | 1/2013 |
| JP | 2013-212184 | 10/2013 |
| JP | 2015-32061 A | 2/2015 |
| JP | 2015-93120 A | 5/2015 |
| JP | 2015-211801 | 11/2015 |
| JP | 2016-087020 | 5/2016 |
| JP | 2016-202940 A | 12/2016 |
| JP | 2017-104534 | 6/2017 |
| JP | 2017-224356 | 12/2017 |
| JP | 6251239 | 12/2017 |

\* cited by examiner

ULTRASONIC DIAGNOSTIC APPARATUS, AND MEDICAL DATA PROCESSING APPARATUS

CROSS-REFERENCE TO RELATED APPLICATION

This application is based upon and claims the benefit of priority from Japanese Patent Application No. 2018-085036, filed on Apr. 26, 2018, and Japanese Patent Application No. 2019-076786, filed on Apr. 15, 2019, the entire contents of each of which are incorporated herein by reference.

FIELD

An embodiment as an aspect of the present invention relates to an ultrasonic diagnostic apparatus and a medical data processing apparatus.

BACKGROUND

In the medical field, an ultrasonic diagnostic apparatus is used for imaging the inside of a subject using ultrasonic waves generated by multiple transducers (piezoelectric transducers) of an ultrasonic probe. The ultrasonic diagnostic apparatus causes the ultrasonic probe, which is connected to the ultrasonic diagnostic apparatus, to transmit ultrasonic waves into the subject, generates an echo signal based on a reflected wave, and obtains a desired ultrasonic image by image processing.

The ultrasonic diagnostic apparatuses are roughly classified into portable ultrasonic diagnostic apparatuses and stationary ultrasonic diagnostic apparatuses according to whether they are portable or not. The portable ultrasonic diagnostic apparatus is also referred to as a tablet-type ultrasonic diagnostic apparatus, and is often used at a round-visit in a hospital because of its excellent portability relative to the conventional stationary ultrasonic diagnostic apparatus. At the round-visit, an operator such as a doctor performs an ultrasonic scan (synonymous with "ultrasonic imaging") for hospitalized patients using the portable ultrasonic diagnostic apparatus. At the same time, the operator confirms the condition of the hospitalized patient on the basis of various items such as condition of vital and drip infusion, and the presence or absence of defecation.

DETAILED DESCRIPTION

An ultrasonic diagnostic apparatus and a medical data processing apparatus according to a present embodiment will be described with reference to the accompanying drawings.

The ultrasonic diagnostic apparatus according to a present embodiment includes processing circuitry. The processing circuitry is configured to: acquire at least one of optical image data and sound data as data related to a confirmation item corresponding to a disorder name of a subject or an examination type for an ultrasonic scan; associate the ultrasonic image data acquired by the ultrasonic scan with the data related to the confirmation item; and store the association in a memory.

1. Ultrasonic Diagnostic Apparatus

Figure 1:
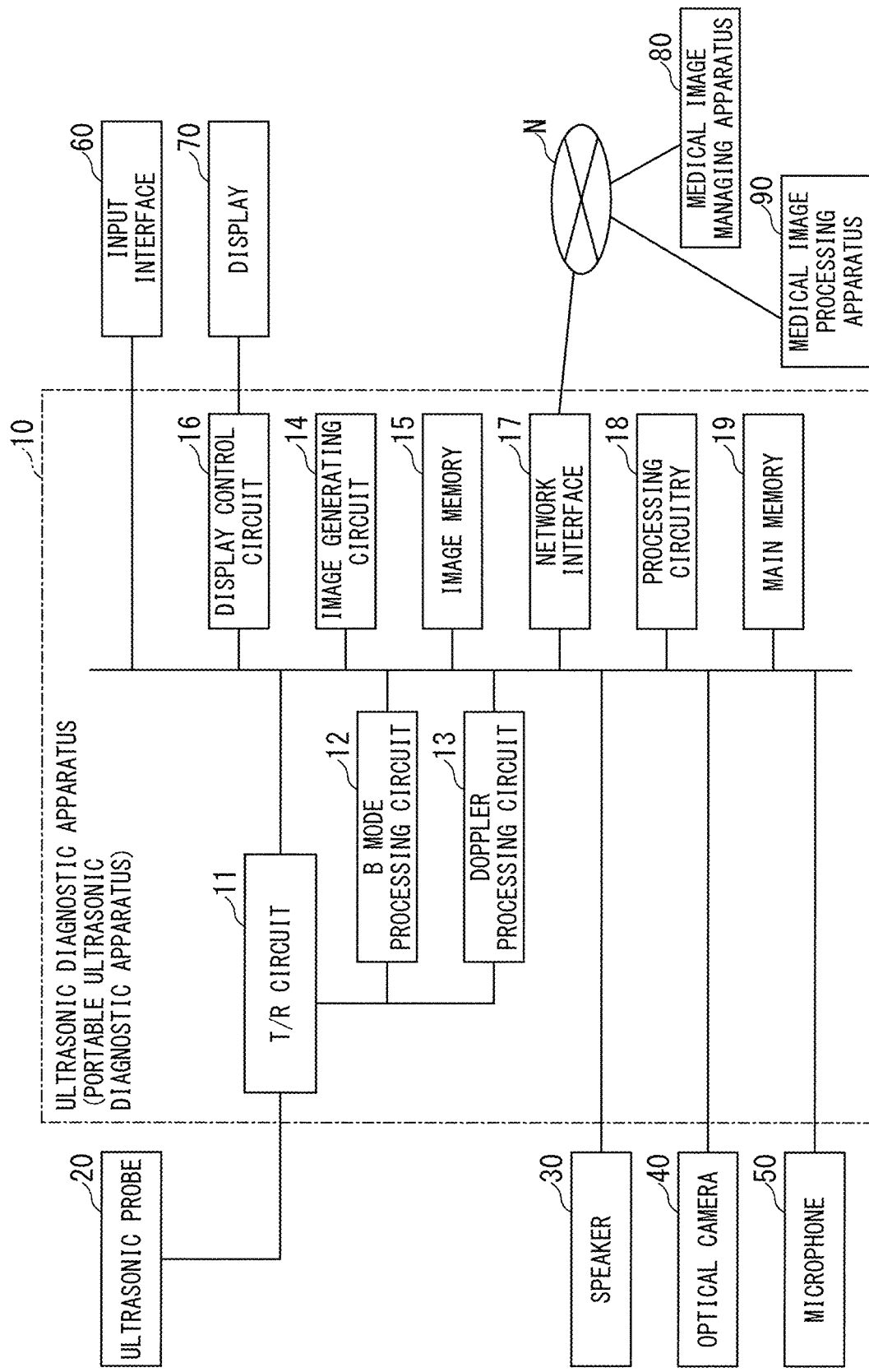
FIG. 1 is a schematic diagram showing a configuration of an ultrasonic diagnostic apparatus according to a present embodiment.

FIG. 1 is a schematic diagram showing a configuration of an ultrasonic diagnostic apparatus according to a present embodiment.

FIG. 1 shows an ultrasonic diagnostic apparatus 10 according to a present embodiment. FIG. 1 shows an ultrasonic probe 20, a speaker 30, an optical camera 40, a microphone 50, an input interface 60, and a display 70. It should be noted that a device in which at least one of the ultrasonic probe 20, the speaker 30, the optical camera 40, the microphone 50, the input interface 60, and the display 70 is added to the ultrasonic diagnostic apparatus 10 may be referred to as an ultrasonic diagnostic apparatus in some cases. In the following description, a case where all of the ultrasonic probe 20, the speaker 30, the optical camera 40, the microphone 50, the input interface 60, and the display 70 are provided outside the ultrasonic diagnostic apparatus 10 will be described.

The ultrasonic diagnostic apparatus 10 are roughly classified into a portable ultrasonic diagnostic apparatuses or a stationary ultrasonic diagnostic apparatus according to whether they are portable or not. The portable ultrasonic diagnostic apparatus is also referred to as a tablet-type ultrasonic diagnostic apparatus, and is often used at a round-visit in a hospital because of its excellent portability relative to the conventional stationary ultrasonic diagnostic apparatus. The ultrasonic diagnostic apparatus 10 may be a portable ultrasonic diagnostic apparatus or a stationary ultrasonic diagnostic apparatus.

The ultrasonic diagnostic apparatus 10 includes a transmitting/receiving (T/R) circuit 11, a B mode processing circuit 12, a Doppler processing circuit 13, an image generating circuit 14, an image memory 15, a display control circuit 16, a network interface 17, processing circuitry 18, and a main memory 19. The circuits 11 to 14 are configured by an application specific integrated circuit (ASIC) or the like. However, the present invention is not limited to this case, and all or a part of the functions of the circuits 11 to 14 may be realized by the processing circuitry 18 executing a program.

The T/R circuit 11 has a transmitting circuit and a receiving circuit (not shown). Under the control of the processing circuitry 18, the T/R circuit 11 controls transmission directivity and reception directivity in transmission and reception of ultrasonic waves. The case where the T/R circuit 11 is provided in the ultrasonic diagnostic apparatus 10 will be described, but the T/R circuit 11 may be provided in the ultrasonic probe 20, or may be provided in both of the ultrasonic diagnostic apparatus 10 and the ultrasonic probe 20. The T/R circuit 11 is an example of a T/R unit.

The transmitting circuit has a pulse generating circuit, a transmission delay circuit, a pulsar circuit and the like, and supplies a drive signal to ultrasonic transducers. The pulse generating circuit repeatedly generates a rate pulse for forming a transmission ultrasonic wave at a predetermined rate frequency. The transmission delay circuit converges the ultrasonic waves generated from the ultrasonic transducer of the ultrasonic probe 20 into a beam shape, and gives a delay time for each piezoelectric transducer necessary for determining the transmission directivity to each rate pulse generated by the pulse generating circuit. In addition, the pulsar circuit applies a drive pulse to the ultrasonic transducers at a timing based on the rate pulse. The transmission delay circuit arbitrarily adjusts the transmission direction of the ultrasonic beam transmitted from a piezoelectric transducer surface by changing the delay time given to each rate pulse.

The receiving circuit has an amplifier circuit, an analog to digital (A/D) converter, an adder, and the like, and receives the echo signal received by the ultrasonic transducers and performs various processes on the echo signal to generate echo data. The amplifier circuit amplifies the echo signal for each channel, and performs gain correction processing. The A/D converter A/D-converts the gain-corrected echo signal, and gives a delay time necessary for determining the reception directivity to the digital data. The adder adds the echo signal processed by the A/D converter to generate echo data. By the addition processing of the adder, the reflection component from the direction corresponding to the reception directivity of the echo signal is emphasized.

The B mode processing circuit 12 receives, under the control of the processing circuitry 18, the echo data from the receiving circuit, performs logarithmic amplification, envelope detection processing and the like, thereby generating data (two-dimensional or three-dimensional data) whose signal intensity is represented by brightness of luminance. This data is generally called B mode data. The B mode processing circuit 12 is an example of a B mode processing unit.

The Doppler processing circuit 13 frequency-analyzes, under the control of the processing circuitry 18, the phase information from the echo data from the receiving circuit, and extracts the blood flow or tissue due to the Doppler effect, thereby generating data (two-dimensional or three-dimensional data) obtained by extracting moving state information such as average speed, dispersion, power and the like for multiple points. This data is generally called Doppler data. The Doppler processing circuit 13 is an example of a Doppler processing unit.

The image generating circuit 14 generates, under the control of the processing circuitry 18, an ultrasonic image expressed in a predetermined luminance range as image data based on the echo signal received by the ultrasonic probe 20. For example, the image generating circuit 14 generates a B mode image in which the intensity of the reflected wave is expressed in luminance from the two-dimensional B mode data generated by the B mode processing circuit 12 as the ultrasonic image. Further, the image generating circuit 14 generates, as the ultrasonic image, a color Doppler image representing moving state information from the two-dimensional Doppler data generated by the Doppler processing circuit 13 such as an average velocity image, a dispersed image, a power image, or a combined image thereof. The image generating circuit 14 is an example of an image generating unit.

The image memory 15 includes memory cells in two axial directions per frame, and includes a two-dimensional memory which is a memory having the memory cells for frames. Under the control of the processing circuitry 18, the two-dimensional memory as the image memory 15 stores the ultrasonic image of one frame or the ultrasonic images frames generated by the image generating circuit 14 as two-dimensional image data. The image memory 15 is an example of a storage unit.

The image generating circuit 14 performs, under the control of the processing circuitry 18, three-dimensional reconstruction on the ultrasonic image arranged in the two-dimensional memory as the image memory 15, if necessary, by interpolation processing, thereby generating an ultrasonic image as volume data in a three-dimensional memory as the image memory 15. As an interpolation processing method, a known technique is used.

The image memory 15 may include a three-dimensional memory which is a memory having memory cells in three axial directions (X-axis, Y-axis, and Z-axis direction). The three-dimensional memory as the image memory 15 stores the ultrasonic image generated by the image generating circuit 14 as volume data under the control of the processing circuitry 18.

The display control circuit 16 includes a graphics processing unit (GPU), a Video RAM (VRAM), and the like. Under the control of the processing circuitry 18, the display control circuit 16 displays the ultrasonic image (for example, a live image), requested for display output from the processing circuitry 18, to the display 70. The display control circuit 16 is an example of a display control unit.

The network interface 17 implements various information communication protocols according to the form of the network. In accordance with these various protocols, the network interface 17 connects the ultrasonic diagnostic apparatus 10 and other devices such as the external medical image managing apparatus 80 and the medical image processing apparatus 90. As this connection, electrical connection or the like via an electronic network can be applied. In this embodiment, the electronic network means the whole information communication network using the telecommunication technology, and includes a local area network (LAN) of a wireless/wired hospital core and an internet network, a telephone communication network, an optical fiber communication network, a cable communication network, a satellite communication network, and the like. When the ultrasonic diagnostic apparatus 10 is a portable ultrasonic diagnostic apparatus, the portable ultrasonic diagnostic apparatus as a wireless LAN client (wireless terminal) is connected to the network N via an access point (not shown) which is a wireless device.

Further, the network interface 17 may implement various protocols for non-contact wireless communication. In this case, the ultrasonic diagnostic apparatus 10 can directly exchange data with the ultrasonic probe 20, for example, without going through the network. The network interface 17 is an example of a network connection unit.

The processing circuitry 18 means an ASIC, a programmable logic device, etc. in addition to a dedicated or general purpose central processing unit (CPU), a micro processor unit (MPU), or graphics processing unit (GPU). A representative example of the programmable logic device is a simple programmable logic device (SPLD), a complex programmable logic device (CPLD), or a field programmable gate array (FPGA).

Further, the processing circuitry 18 may be constituted by a single circuit or a combination of independent circuit elements. In the latter case, the main memory 19 may be provided individually for each circuit element, or a single main memory 19 may store programs corresponding to the functions of the circuit elements. The processing circuitry 18 is an example of a processing unit.

The main memory 19 is constituted by a semiconductor memory element such as a random access memory (RAM), a flash memory, a hard disk, an optical disk, or the like. The main memory 19 may be constituted by a portable medium such as a universal serial bus (USB) memory and a digital video disk (DVD). The main memory 19 stores various processing programs (including an OS (operating system) and the like besides the application program) used in the processing circuitry 18 and data necessary for executing the programs. In addition, the OS may include a graphical user interface (GUI) which allows the operator to frequently use graphics to display information on the display 70 to the operator and can perform basic operations by the input interface 60. The main memory 19 is an example of a storage unit.

The ultrasonic probe 20 includes microscopic transducers (piezoelectric elements) on the front surface portion, and transmits and receives ultrasonic waves to a region including a scan target, for example, a region including a lumen. Each transducer is an electroacoustic transducer, and has a function of converting electric pulses into ultrasonic pulses at the time of transmission and converting reflected waves to electric signals (reception signals) at the time of reception. The ultrasonic probe 20 is configured to be small and lightweight, and is connected to the ultrasonic diagnostic apparatus 10 via a cable (or wireless communication).

The ultrasonic probe 20 is classified into types such as a linear type, a convex type, a sector type, etc., depending on a difference in scanning system. The ultrasonic probe 20 is classified into a 1D array probe in which transducers are arrayed in a one-dimensional (1D) manner in the azimuth direction, and a 2D array probe in which transducers are arrayed in two dimensions (2D) manner in the azimuth direction and in the elevation direction, depending on the array arrangement dimension. The 1D array probe includes a probe in which a small number of transducers are arranged in the elevation direction.

In this embodiment, when a 3D scan, that is, a volume scan is executed, the 2D array probe having a scan type such as the linear type, the convex type, the sector type, or the like is used as the ultrasonic probe 20. Alternatively, when the volume scan is executed, the 1D probe having a scan type such as the linear type, the convex type, the sector type and the like and having a mechanism that mechanically oscillates in the elevation direction is used as the ultrasonic probe 20. The latter probe is also called a mechanical 4D probe.

The speaker 30 receives an electric signal from the processing circuitry 18, converts the electric signal to physical vibration, and outputs music, voice, and the like. The speaker 30 is an example of a sound output unit.

The optical camera 40 includes an optical system for forming an image. Under control of the processing circuitry 18, the optical camera 40 captures a subject, collects optical image data (for example, still image data and dynamic image data), and transmits the optical image data to the processing circuitry 18. The optical camera 40 is an example of an image generating unit.

Under the control of the processing circuitry 18, the microphone 50 receives the sound (air vibration), converts the sound into an electric signal, and transmits the electric signal to the processing circuitry 18. The microphone 50 is an example of a sound collecting unit.

The input interface 60 includes an input device operable by an operator, and a circuit for inputting a signal from the input device. The input device may be a trackball, a switch, a mouse, a keyboard, a touch pad for performing an input operation by touching an operation surface, a touch screen in which a display screen and a touch pad are integrated, a non-contact input circuit using an optical sensor, an audio input circuit, and the like. When the input device is operated by the operator, the input interface 60 generates an input signal corresponding to the operation and outputs it to the processing circuitry 18. The input interface 60 is an example of an input unit.

The display 70 is constituted by a general display output device such as a liquid crystal display or an organic light emitting diode (OLED) display. The display 70 displays various kinds of information under the control of the processing circuitry 18. The display 70 is an example of a display unit.

FIG. 1 shows the medical image managing apparatus 80 and the medical image processing apparatus 90 which are external devices of the ultrasonic diagnostic apparatus 10. The medical image managing apparatus 80 is, for example, a digital imaging and communications in medicine (DICOM) server, and is connected to a device such as the ultrasonic diagnostic apparatus 10 so that data can be transmitted and received via the network N. The medical image managing apparatus 80 manages a medical image such as an ultrasonic image generated by the ultrasonic diagnostic apparatus 10 as a DICOM file.

The medical image processing apparatus 90 is connected to devices such as the ultrasonic diagnostic apparatus 10 and the medical image management apparatus 50 so that data is transmitted and received via the network N. An Example of the medical image processing apparatus 90 includes a workstation that performs various image processing on the ultrasonic image generated by the ultrasonic diagnostic apparatus 10, a portable information processing terminal such as a tablet terminal, and an image interpreting terminal for displaying an ultrasonic image data as an ultrasonic image and performing a doctor's image interpreting. It should be noted that the medical image processing apparatus 90 is an offline apparatus and may be an apparatus capable of reading ultrasonic image data generated by the ultrasonic diagnostic apparatus 10 via a portable storage medium.

Subsequently, functions of the ultrasonic diagnostic apparatus 10 will be described.

Figure 2:
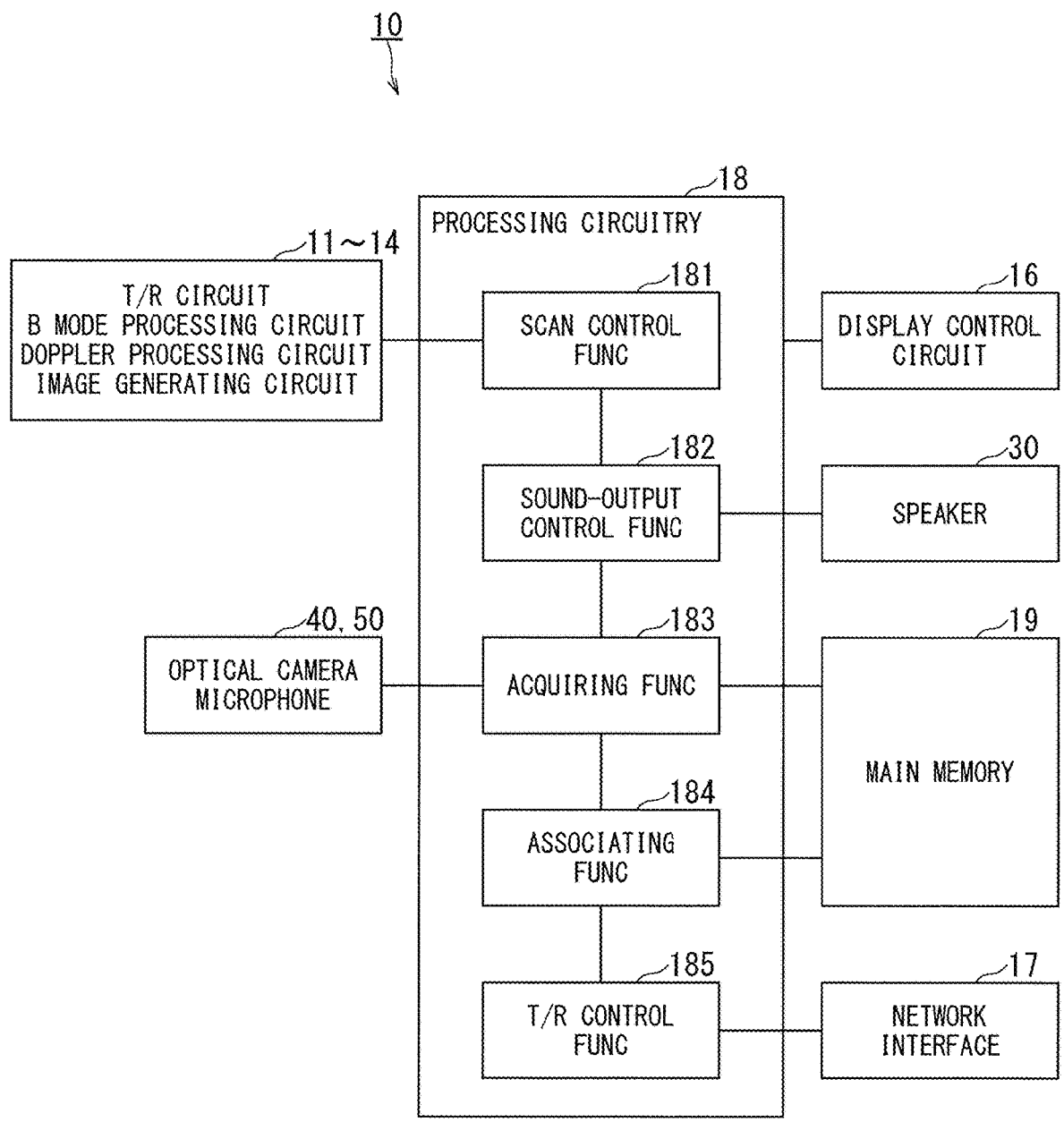
FIG. 2 is a block diagram showing functions of the ultrasonic diagnostic apparatus according to the present embodiment.

FIG. 2 is a block diagram showing functions of the ultrasonic diagnostic apparatus 10.

The processing circuitry 18 reads out and executes a program stored in the main memory 19 or directly incorporated in the processing circuitry 18, thereby realizing a scan control function 181, a sound-output control function 182, an acquiring function 183, an associating function 184, and a transmitting/receiving (T/R) control function 185. Hereinafter, a case where the functions 181 to 185 function as software will be described as an example. All or a part of the functions 181 to 185 may be provided as a circuit or the like of ASIC etc. in the ultrasonic diagnostic apparatus 10.

The scan control function 181 includes a function of controlling the T/R circuit 11, the B mode processing circuit 12, the Doppler processing circuit 13, the image generating circuit 14 and the like to execute an ultrasonic scan using the ultrasonic probe 20, and thereby generating ultrasonic image data. The scan control function 181 is an example of a scan control unit.

The sound-output control function 182 includes a function of controlling an output of sound data for instructing collection of evidence data corresponding to a confirmation item related to a diagnostic action or treatment action on a patient. According to a disorder name or an examination type etc., the confirmation item is previously determined for every hospital. Therefore, the sound-output control function 182 acquires one or more appropriate confirmation items in accordance with the disorder name of the corresponding patient or the examination type, and appropriately outputs the sound data indicating the acquired confirmation items. The confirmation items include information such as condition of vital and drip infusion, presence or absence of bowel movement, etc., according to the disorder name of the corresponding patient or the examination type. The vital is also called a vital sign, and refers to at least one piece of information of electrocardiogram, pulse, heart rate, respiratory rate, blood pressure, and temperature. The sound-output control function 182 is an example of a sound-output control unit.

The acquiring function 183 includes a function of acquiring evidence data indicating evidence of a diagnostic action or a treatment action, the evidence corresponding to a confirmation item related to a diagnostic action or a treatment action on a patient. For example, the acquiring function 183 acquires optical image data from the optical camera 40 as the evidence data. Also, for example, the acquiring function 183 acquires sound data from the microphone 50 as the evidence data. The evidence data includes at least one of the optical image data and the sound data. The acquiring function 183 is an example of an acquiring unit.

The associating function 184 includes a function of associating the ultrasonic image data acquired by the ultrasonic scan with the evidence data, and storing the association in the main memory 19. As a first example, the associating function 184 associates the ultrasonic image data generated by the scan control function 181 with the evidence data acquired by the acquiring function 183 to generate associated data, and stores the associated data in the main memory 19. As a second example, the associating function 184 converts the evidence data from a non-DICOM format to a DICOM format, and stores the ultrasonic image data generated by the scan control function 181 and the evidence data both in the DICOM format in the main memory 19. Hereinafter, the first example will be described unless otherwise stated. The associating function 184 is an example of an associating unit.

The T/R control function 185 transmits the associated data generated by the associating function 184 to an external apparatus such as the medical image processing apparatus (for example, the image interpreting terminal) 90, and receives sound data corresponding to the associated data from the external apparatus. The sound-output control function 182 can also control an output of the sound data received by the T/R control function 185. The T/R control function 185 is an example of T/R control unit.

2. First Example of Operation of Ultrasonic Diagnostic Apparatus 10

Figure 3:
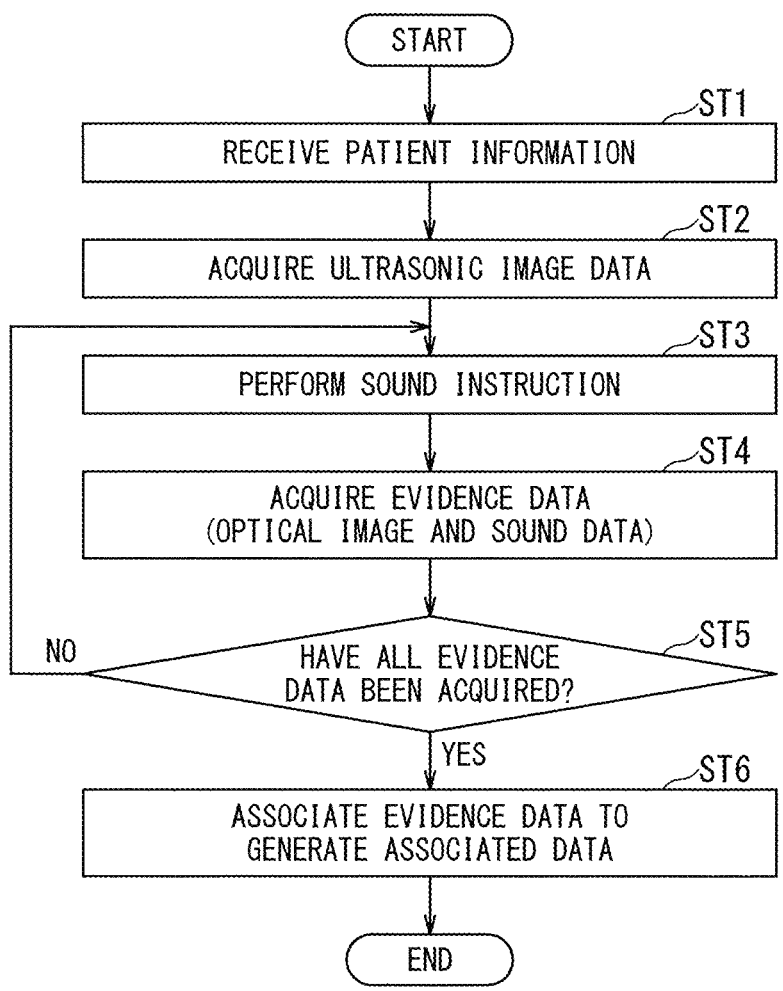
FIG. 3 is a diagram showing a first example of an operation of the ultrasonic diagnostic apparatus according to the present embodiment as a flowchart.

FIG. 3 is a diagram showing a first example of an operation of the ultrasonic diagnostic apparatus 10 as a flowchart. In FIG. 3, reference numerals with numbers attached to "ST" indicate steps in the flowchart.

The scan control function 181 receives patient information of a patient who is scheduled to undergo an examination (step ST1). The patient information includes information such as patient identification information such as patient identification (ID), patient's gender, disorder name and the like. Acceptance of the patient information may be in response to an instruction from the operator via the input interface 60, or may be in response to an examination order from an examination order apparatus such as a modality worklist management (MWM) server. The scan control function 181 controls the T/R circuit 11, the B mode processing circuit 12, the Doppler processing circuit 13, the image generating circuit 14 and the like according to a scan start instruction from the operator via the input interface 60, executes an ultrasonic scan to generate ultrasonic image data, and acquires the ultrasonic image data (step ST2).

The sound-output control function 182 outputs, as the sound data, a confirmation item related to a diagnosis action or a treatment action on the corresponding patient from the speaker 30 according to the disorder name included in the patient information of the corresponding patient (step ST3). For example, in step ST3, the sound-output control function 182 performs a sound instruction "Please take a picture of condition of drip infusion" from the speaker 30.

At the time of round-visit in the hospital, the operator operating the ultrasonic diagnostic apparatus 10 needs to confirm many items per hospitalized patient. In addition, confirmation items differ from each hospitalized patient. Therefore, the work of the operator is complicated. If the confirmation item for the hospitalized patient is missing, it is necessary to make a diagnosis for the same hospitalized patient again, leading to a decrease in the diagnostic efficiency. However, according to step ST3, the confirmation item necessary for each hospitalized patient is provided by sound, so that the diagnosis efficiency is improved in the case of the round-visit in the hospital.

Figure 4:
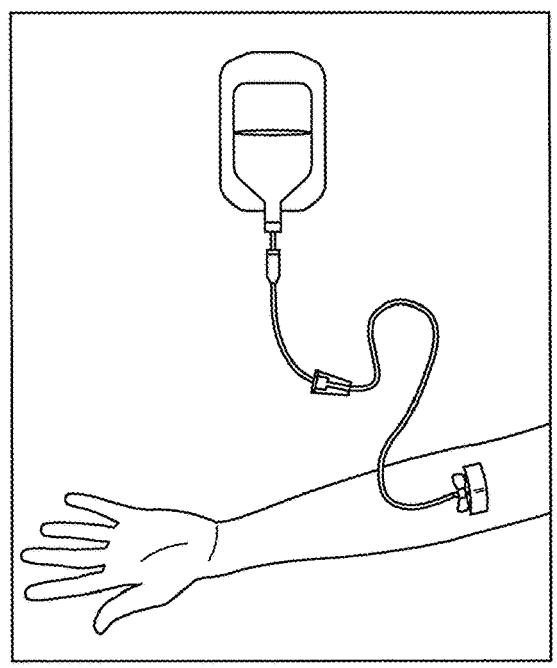
FIG. 4 is a diagram showing optical image data as an example of evidence data acquired by the first example of the operation of the ultrasonic diagnostic apparatus according to the present embodiment.

The operator collects the evidence data corresponding to the confirmation item of the patient using the optical camera 40 or the microphone 50 according to the sound instruction in step ST3, so the acquiring function 183 acquires evidence data corresponding to the output confirmation item (step ST4). Specifically, the operator captures an "drip infusion (bottle)" using the optical camera 40 in response to the sound instruction "Please take a picture of condition of drip infusion" in step ST3, so the acquiring function 183 acquires optical image data in which "drip infusion (bottle)" appears as evidence data corresponding to the sound instruction. FIG. 4 is a diagram showing optical image data as an example of the evidence data acquired in step ST4.

Returning to the explanation of FIG. 3, the acquiring of the evidence data is completed in step ST4, and the operator operates the input interface 60 to instruct "next", so the acquiring function 183 determines whether or not all the confirmation items corresponding to the disorder name have been confirmed for the corresponding patient, that is, all the evidence data corresponding to the disorder name has been acquired (step ST5). If it is determined as "YES" in step ST5, that is, if it is determined that all the evidence data have been acquired for the corresponding patient, the associating function 184 associates the ultrasonic image data, acquired in step ST2 and associated with the patient information, with the evidence data acquired in step ST4 to generate associated data (shown in FIG. 6) (step ST6). Then, the associating function 184 stores the associated data in the main memory 19.

If it is determined as "NO" in step ST5, that is, if it is determined that all the evidence data has not been acquired, the sound-output control function 182 outputs, from the speaker 30, sound data for instructing acquisition of the next evidence data (step ST3). For example, in step ST3, the sound-output control function 182 performs a sound instruction "Please take a picture of condition of vital" from the speaker 30. The vitals are usually displayed on the display 70.

Figure 5:
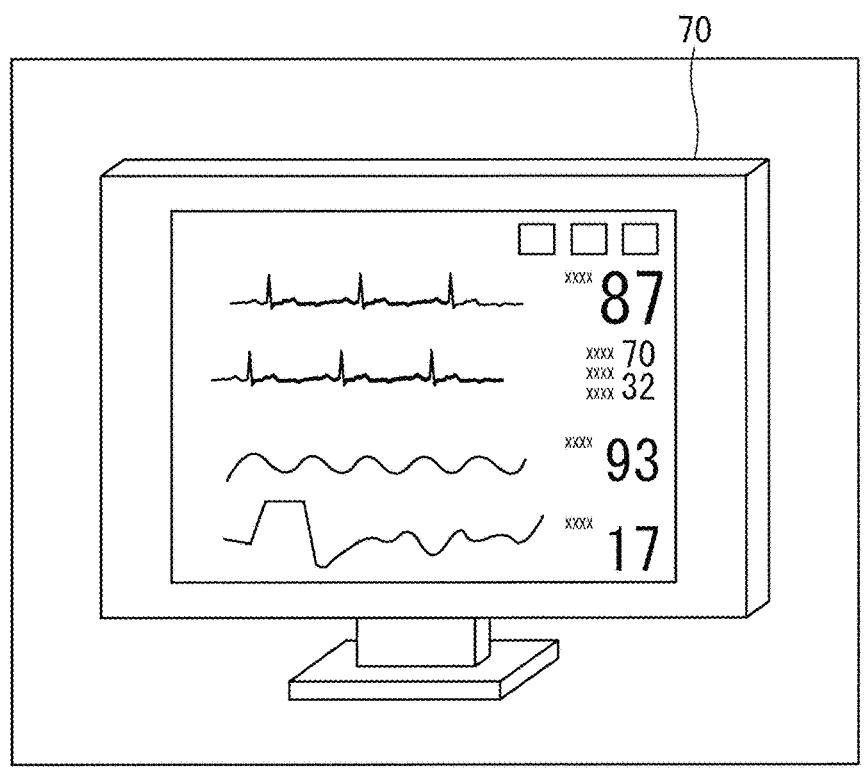
FIG. 5 is a diagram showing optical image data as an example of evidence data acquired by the first example of the operation of the ultrasonic diagnostic apparatus according to the present embodiment.

The operator captures the "display 70" using the optical camera 40 in response to the sound instruction "Please take a picture of condition of vital" in step ST3, so the acquiring function 183 acquires optical image data in which the "display" is captured as evidence data corresponding to the sound instruction. FIG. 5 is a diagram showing optical image data as an example of the evidence data acquired in step ST4.

Figure 6:
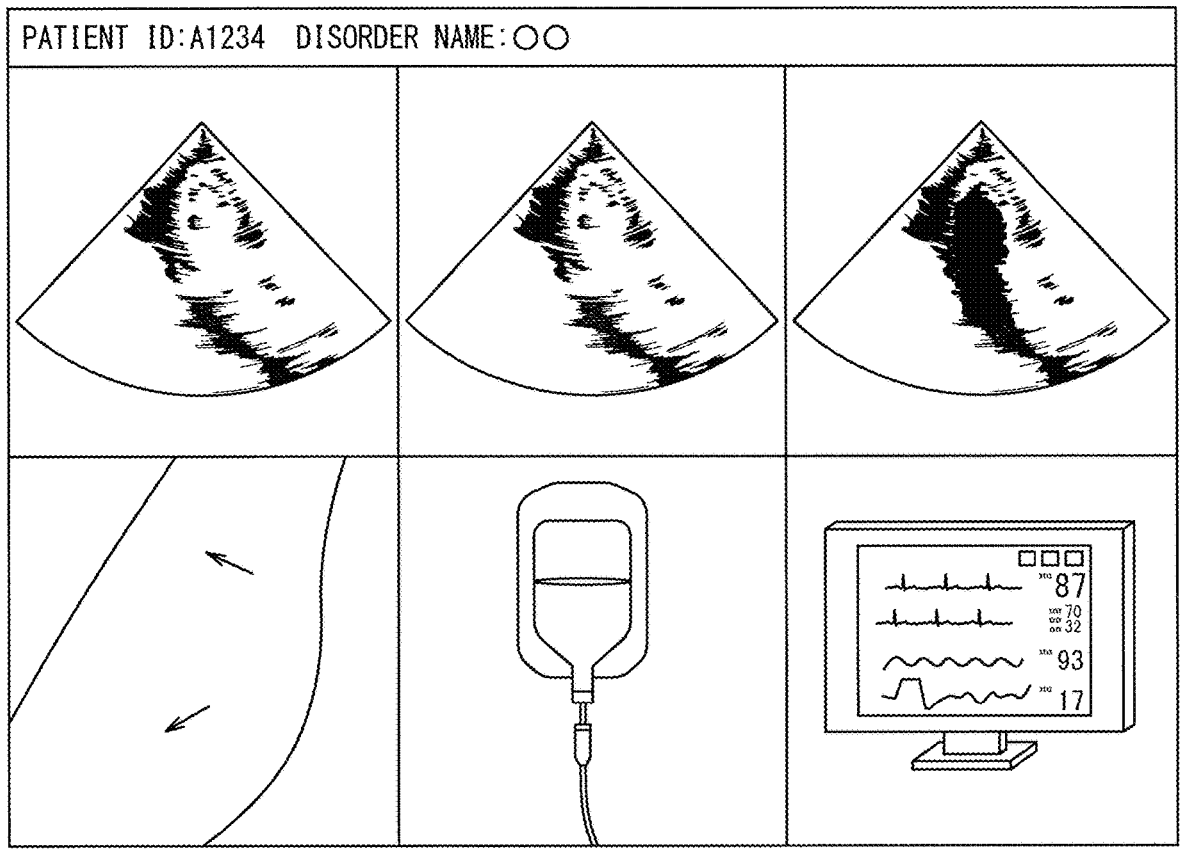
FIG. 6 is a diagram showing an example of associated data in the first example of the operation of the ultrasonic diagnostic apparatus according to the present embodiment.

FIG. 6 is a diagram showing an example of the associated data.

FIG. 6 shows the patient ID "A1234" included in the patient information and the associated data of the patient related to the disease name "oo" included in patient information. The patient information is acquired from tag data of a DICOM format-ultrasonic image data. The upper part of the associated data shown in FIG. 6 shows three pieces of ultrasonic image data related to the patient related to the patient ID "A1234". The lower part of the associated data shown in FIG. 6 shows three pieces of evidence data related to the patient related to the patient ID "A1234". The three pieces of evidence data include optical image data of one leg related to the patient ID "A1234" shown in lower-left side, optical image data indicating a condition of a drip infusion shown in lower-center, and optical image data indicating a condition of vital shown in lower-right side. The evidence data may include sound data, but it is not shown.

The associated data includes ultrasonic image data in the DICOM format and the evidence data in a non-DICOM format. The associating function 184 preferably manages the associated data as a system different from the system managed using the DICOM.

As described above, according to the associated data, the ultrasonic diagnostic apparatus 10 centrally manages, as the associated data for each patient, the diagnostic image of the corresponding patient and the three pieces of evidence data (optical image data, etc.) corresponding to the disorder name. The diagnostic image corresponds to the DICOM data, and the evidence data corresponds to the non-DICOM data.

On the other hand, as described above, the associating function 184 of the ultrasonic diagnostic apparatus 10 can also perform an aspect of associating the ultrasonic image data with the evidence data without generating the associated data. For example, the associating function 184 can convert a non-DICOM format evidence data generated in a unique format into the DICOM format, and store both the ultrasonic image data and the evidence data in the DICOM format in the main memory 19. The associating function 184 performs a DICOM conversion by attaching the patient information required by the DICOM standard as the tag data to the optical image data and the sound data which are the evidence data, and stores the attached evidence data in the DICOM format in the main memory 19. The associating function 184 may attach patient data corresponding to an active ultrasonic examination to the evidence data acquired during the ultrasonic examination.

As described above, according to the DICOM conversion of the non-DICOM format evidence data, the ultrasonic diagnostic apparatus 10 can centrally manage, based on the tag data, the diagnostic image and the evidence data in the DICOM format of the corresponding patient.

According to the first example of the operation of the ultrasonic diagnostic apparatus 10, the confirmation item necessary for each patient are provided by sound according to the disorder type, so it is possible to improve the diagnostic efficiency in the case of the round-visit in a hospital. Further, according to the first example of the operation of the ultrasonic diagnostic apparatus 10, the associated data including the evidence data is generated on a patient-by-patient basis, so it is possible to centrally manage the evidence in which the confirmation item has been confirmed together with the diagnostic image.

3. Second Example of Operation of Ultrasonic Diagnostic Apparatus 10

The second example of an operation of the ultrasonic diagnostic apparatus 10 transmits the associated data generated in step ST6 of FIG. 3 to an external apparatus, and receives and outputs sound data corresponding to the associated data from the external apparatus.

Figure 7:
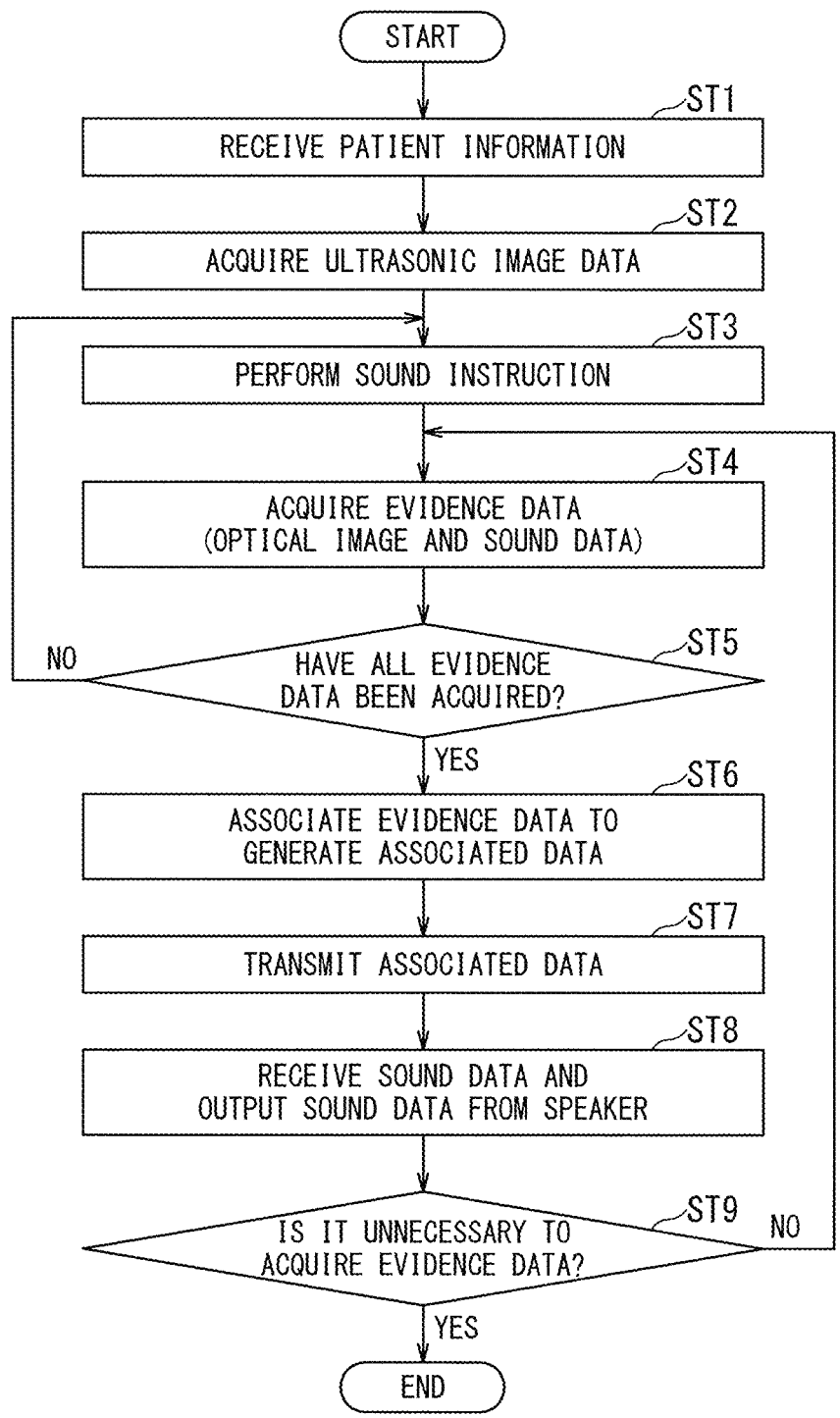
FIG. 7 is a diagram showing a second example of an operation of the ultrasonic diagnostic apparatus according to the present embodiment as a flowchart.

FIG. 7 is a diagram showing a second example of an operation of the ultrasonic diagnostic apparatus 10 as a flowchart. In FIG. 7, reference numerals with numbers attached to "ST" indicate steps in the flowchart.

The T/R control function 185 transmits the associated data generated in step ST6 to an external apparatus such as a medical image processing apparatus (for example, an image interpreting terminal) 90 (step ST7). The T/R control function 185 receives sound data corresponding to the associated data from the image interpreting terminal 90, and the sound-output control function 182 outputs the received sound data from the speaker 30 (step ST8).

The associated data relating to the corresponding patient is transmitted to the image interpreting terminal 90 operated by another doctor (for example, an image interpreter) during the round-visit in step ST7, and the sound data indicating the opinion and instructions of the image interpreter is output from the speaker 30 in real time in step ST8. Thus, it is possible for the operator of the ultrasonic diagnostic apparatus 10 to diagnose the corresponding patient according to the instruction of the image interpreter. This enables diagnostic feedback on the spot during round-visit, resulting in improved diagnostic efficiency.

In addition, the instruction of acquisition of additional evidence data or re-acquisition of evidence data from the image interpreter may be output from the speaker 30 in step ST8. In that case, it is possible for the operator of the ultrasonic diagnostic apparatus 10 to acquire additional evidence data necessary for diagnosis and acquisition of appropriate evidence data. Thus, it is possible to instruct the operator to reacquire not only the evidence data corresponding to the confirmation item set in advance but also the evidence data added by the image interpreter during the round-visit and also the evidence data which is insufficiently acquired.

The acquiring function 183 determines whether it is unnecessary to acquire the evidence data of the patient on the basis of the analysis of the sound data received in step ST8 or the operation of the operator via the input interface 60 (step ST9). If it is determined as "YES" in step ST9, that is, if it is determined that the acquisition of the evidence data related to the corresponding patient is unnecessary, the ultrasonic diagnostic apparatus 10 ends the operation.

If it is determined as "NO" in step ST9, that is, it is determined that the acquisition of the evidence data concerning the patient is necessary, the operator collects the evidence data corresponding to the confirmation item of the patient according to the sound data in step ST8, using optical camera 40 or microphone 50. Thereby, the acquiring function 183 acquires the evidence data corresponding to the output confirmation item (re-acquisition of additional evidence data or evidence data) (step ST4).

According to the second example of the operation of the ultrasonic diagnostic apparatus 10, it is possible to confirm an appropriate confirmation item for each patient according to the instruction from another doctor (for example, image interpreter), and generate the evidence data according to the confirmation item, in addition to the effects of the first example of the operation of the ultrasonic diagnostic apparatus 10. Thus, it is possible to generate an appropriate associated data.

4. Third Example of Operation of Ultrasonic Diagnostic Apparatus 10

The third example of the operation of the ultrasonic diagnostic apparatus 10 is a case which outputs, as sound data, a confirmation item according to an examination type, for example, a stress echo examination, and acquires evidence data corresponding to the confirmation item according to the examination type. The stress echo examination is roughly classified into an exercise echo examination which causes a patient to exercise and a dobutamine stress echo examination which administers a drug to a patient. Any one of the stress echo examinations are an examination which stress the heart with exercise or a drug called dobutamine to confirm changes in movement of the heart muscle and blood flow that are not recognized at rest. In the third example of the operation of the ultrasonic diagnostic apparatus 10, although the case of the exercise stress echo examination will be described, it may be the case of the dobutamine stress echo examination.

Figure 8:
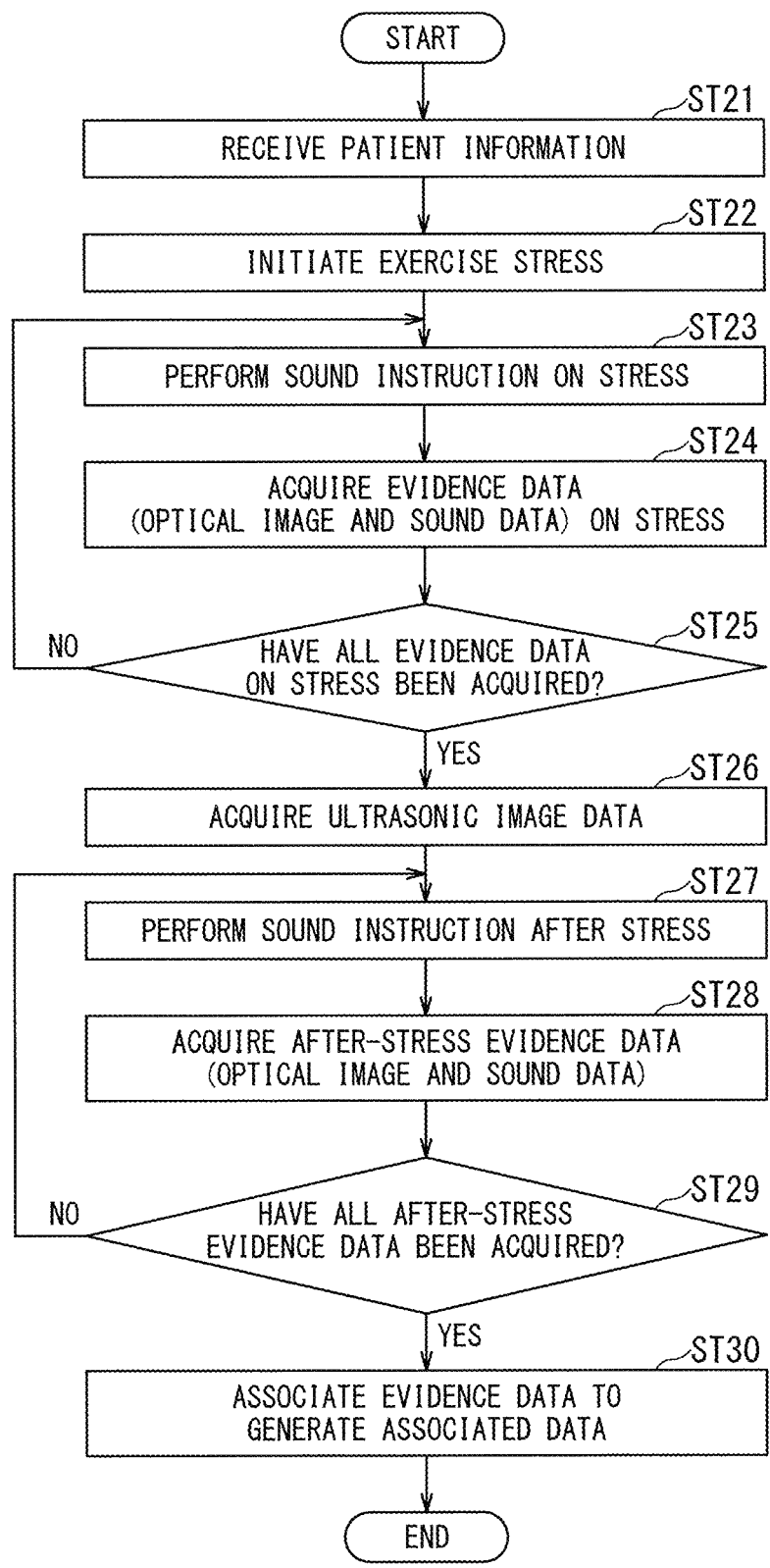
FIG. 8 is a diagram showing a third example of an operation of the ultrasonic diagnostic apparatus according to the present embodiment as a flowchart.

FIG. 8 is a diagram showing a third example of an operation of the ultrasonic diagnostic apparatus 10 as a flowchart. In FIG. 8, reference numerals with numbers attached to "ST" indicate steps in the flowchart.

The scan control function 181 receives patient information of a patient who is scheduled to undergo the stress echo examination (step ST21). Reception of the patient information may be in accordance with an instruction from the operator via the input interface 60, or may be in accordance with an examination order. Then, the exercise stress of the corresponding patient is initiated (step ST22).

The sound-output control function 182 outputs, as the sound data, a confirmation item at the time of the stress related to a diagnosis action or a treatment action on the corresponding patient from the speaker 30 according to the stress echo as the examination type (step ST23). For example, in step ST23, the sound-output control function 182 performs a sound instruction "Please take a picture of condition of exercise under exercise stress" from the speaker 30.

Next, the operator collects the evidence data at the time of the stress corresponding to the confirmation item using the optical camera 40 or the microphone 50 according to the sound data in step ST23, so the acquiring function 183 acquires the evidence data at the time of the stress corresponding to the output confirmation item (step ST24). Specifically, the operator captures an image of the "patient" using the optical camera 40 in response to the sound instruction "Please take a picture of condition of exercise under exercise stress" in step ST23, thereby the acquiring function 183 acquires optical image data in which the "patient" under exercise is shown as the evidence data corresponding to the sound instruction.

The acquiring function 183 determines whether or not all the confirmation items at the time of the stress according to the stress echo have been confirmed for the corresponding patient, that is, all the evidence data at the time of the stress according to the stress echo has been acquired (step ST25). If it is determined as "YES" in step ST25, that is, if it is determined that all the evidence data at the time of the stress has been acquired for the corresponding patient, the scan control function 181 starts an ultrasonic scan from the operator via the input interface 60. According to the instruction, the T/R circuit 11, the B mode processing circuit 12, the Doppler processing circuit 13, the image generating circuit 14 and the like are controlled to start a scan for generating ultrasonic image data and to acquire ultrasonic image data (step ST26).

If it is determined as "NO" in step ST25, that is, if it is determined that all the evidence data at the time of the stress is not acquired, the sound-output control function 182 outputs, from the speaker 30, sound data for instructing acquisition of the evidence data at the time of the stress relating to a diagnostic action or a treatment action (step ST23). For example, in step ST23, the sound-output control function 182 performs a sound instruction "Please take a picture of condition of drip infusion" from the speaker 30 (in the case of the dobutamine stress echo examination).

After completion of the acquisition of the ultrasonic image data, the sound-output control function 182 outputs, as the sound data, an after-stress confirmation item relating to a diagnostic action or a treatment action to the corresponding patient from the speaker 30 according to the stress echo as the examination type (step ST27).

Next, the operator collects the after-stress evidence data corresponding to the confirmation item of the patient using the optical camera 40 or the microphone 50 in response to the sound data in step ST27, thereby the acquiring function 183 acquires the after-stress evidence data (step ST28).

The acquiring function 183 determines whether or not all the after-stress confirmation items corresponding to the stress echo have been confirmed for the corresponding patient, that is, all the after-stress evidence data corresponding to the stress echo has been acquired (step ST29). If it is determined as "YES" in step ST29, that is, it is determined that all the after-stress evidence data has been acquired for the corresponding patient, the associating function 184 associates the ultrasonic image data, acquired in step ST26 and associated with the patient information, with the evidence data acquired in steps ST24 and ST28 to generate associated data (step ST30), and stores the associated data in the main memory 19.

If it is determined as "NO" in step ST29, that is, if it is determined that not all the after-stress evidence data has been acquired, the sound-output control function 182 outputs sound data for instructing acquisition of the after-stress evidence data relating to a diagnostic action or a treatment action from the speaker 30 (step ST27).

It should be noted that the third example of the operation of the ultrasonic diagnostic apparatus 10 can be combined with another example of operation. For example, the third example of the operation of the ultrasonic diagnostic apparatus 10 may be combined with the second example (shown in FIG. 7). Thereby, the ultrasonic diagnostic apparatus 10 transmits the associated data generated in step ST30 to the external apparatus.

According to the third example of the operation of the ultrasonic diagnostic apparatus 10, the confirmation items necessary for each patient are provided by sound according to the examination type, so that the diagnostic efficiency can be improved. Further, according to the third example of the operation of the ultrasonic diagnostic apparatus 10, by generating the associated data including the evidence data on a patient basis, it is possible to centrally manage the evidence in which the confirmation item is confirmed together with the diagnostic image.

5. Fourth Example of Operation of Ultrasonic Diagnostic Apparatus 10

The fourth example of the operation of the ultrasonic diagnostic apparatus 10 utters, as the sound data, a confirmation item according to the examination type, for example, the examination in an emergency mode, and acquires evidence data corresponding to the confirmation item according to the examination type. The emergency mode is, for example, a mode that is employed when treating a patient during transportation by an ambulance, or when treating a patient at a disaster or distress site.

Figure 9:
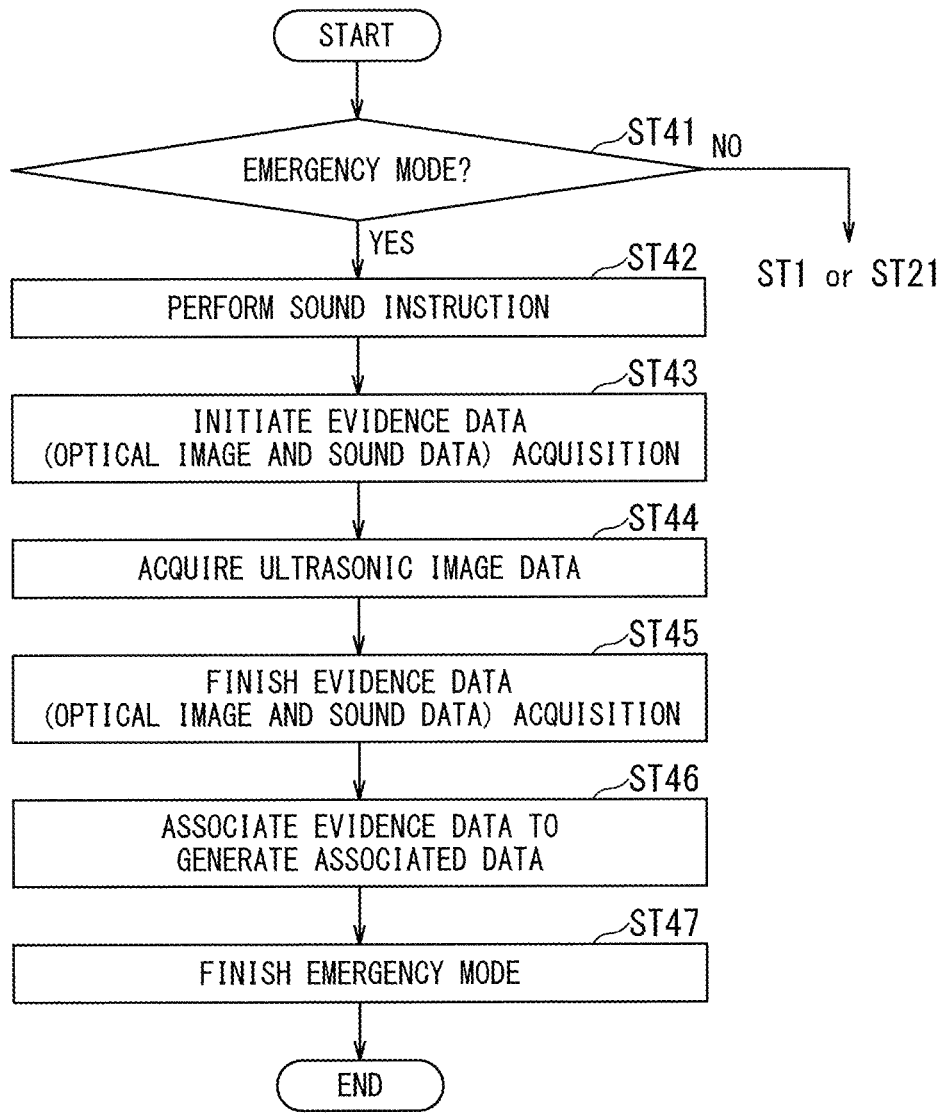
FIG. 9 is a diagram showing a fourth example of an operation of the ultrasonic diagnostic apparatus according to the present embodiment as a flowchart.

FIG. 9 is a diagram showing a fourth example of an operation of the ultrasonic diagnostic apparatus 10 as a flowchart. In FIG. 9, reference numerals with numbers attached to "ST" indicate steps in the flowchart.

The sound-output control function 182 determines whether the confirmation item is not set in advance for the patient who is to perform the examination, and the examination type is an emergency mode (step ST41). If it is determined as "YES" in step ST41, that is, if it is determined that the examination type is in the emergency mode, the sound-output control function 182 outputs, as the sound data, a confirmation item according to the emergency mode and relating to a diagnostic action or a treatment action on the corresponding patient from the speaker 30 before the examination (step ST42). For example, in step ST42, the sound-output control function 182 performs a sound instruction "Please take a dynamic imaging of patient condition" from the speaker 30.

Next, the operator collects the evidence data corresponding to the confirmation item of the patient using the optical camera 40 or the microphone 50 in response to the sound data in step ST42, thereby the acquiring function 183 initiates acquiring the evidence data corresponding to the output confirmation item (step ST43). Specifically, the operator initiates a dynamic-imaging of "patient" using the optical camera 40 in response to the sound data "Please take a dynamic imaging of patient condition" in step ST42, thereby the acquiring function 183 starts acquisition of a dynamic image data in which the "patient" is taken as evidence data corresponding to the sound instruction.

Next, the scan control function 181 controls the T/R circuit 11, the B mode processing circuit 12, the Doppler processing circuit 13, the image generating circuit 14 and the like according to the instruction to start the ultrasonic scan from the operator via the input interface 60 to start the ultrasonic scan, and acquires the ultrasonic image data (step ST44). Then, the acquiring function 183 finishes the acquisition of the evidence data initiated in step ST43 (step ST45).

The associating function 184 associates the ultrasonic image data, acquired in step ST44 and associated with the patient information, with the evidence data acquired in steps ST43 to ST45 to generate associated data (step ST46), and stores the associated data in the memory 19. The ultrasonic diagnostic apparatus 10 finishes the examination in the emergency mode (step ST47).

If it is determined as "NO" in step ST41, that is, if it is determined that the examination type is not the emergency mode, the apparatus 10 proceeds to step ST1 shown in FIG. 3 or 7, or step ST21 shown in FIG. 8.

It should be noted that the fourth example of the operation of the ultrasonic diagnostic apparatus 10 can be combined with another example of operation. For example, the fourth example of the operation of the ultrasonic diagnostic apparatus 10 may be combined with the second example (shown in FIG. 7). Thereby, the ultrasonic diagnostic apparatus 10 transmits the associated data generated in step ST46 to the external apparatus.

According to the fourth example of the operation of the ultrasonic diagnostic apparatus 10, the same effect as the effect of the third example of the operation of the ultrasonic diagnostic apparatus 10 can be obtained. Further, according to the fourth example of the operation of the ultrasonic diagnostic apparatus 10, it is possible to generate the associated data including the dynamic image data and the sound data indicating the patient condition under examination in the emergency mode.

6. First Example of Medical Data Processing Apparatus

Converting the non-DICOM format of the evidence data into the DICOM format and managing the data according to the DICOM format are also possible by a medical data processing apparatus. The medical data processing apparatus is an apparatus capable of receiving the patient information included in an examination order from an examination order apparatus such as an MWM server which issues the examination order.

Figure 10:
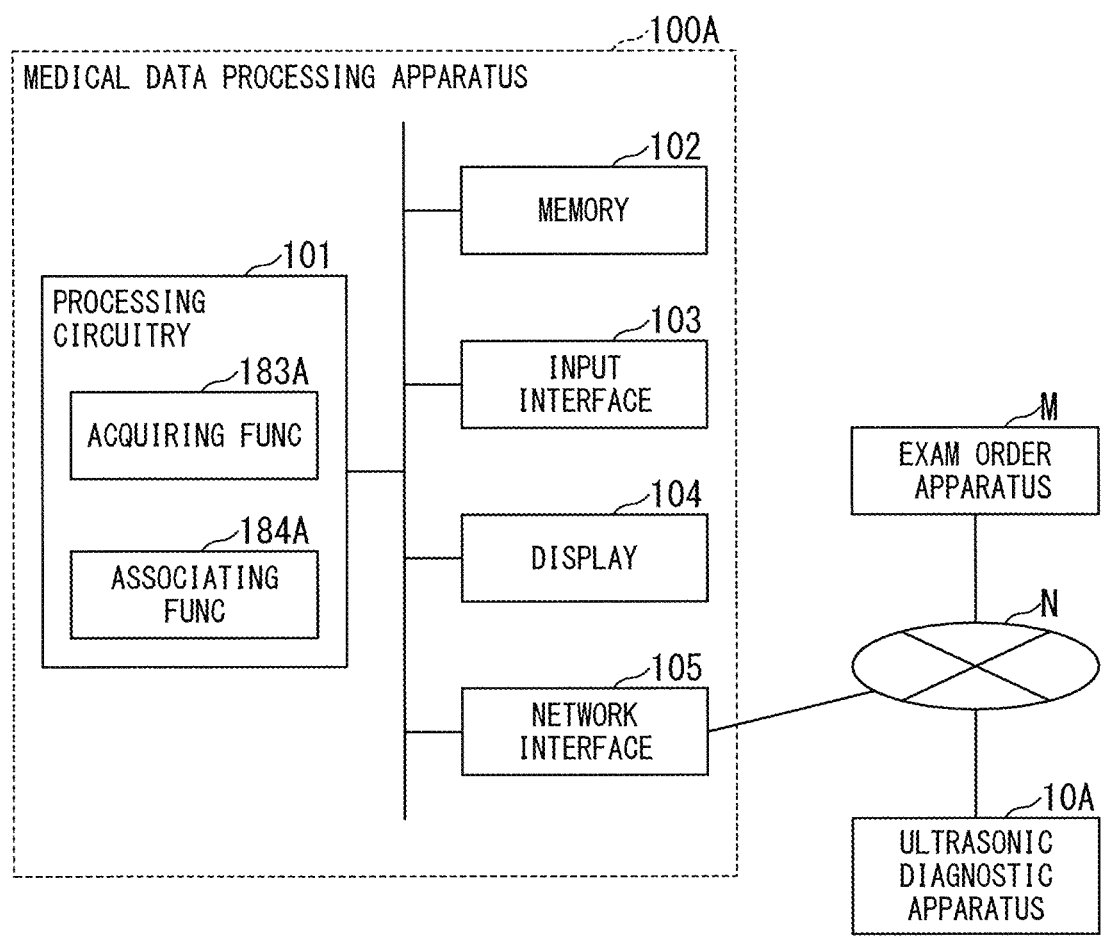
FIG. 10 is a block diagram showing a configuration and functions of a first example of a medical data processing apparatus according to a present embodiment.

FIG. 10 is a block diagram showing a configuration and functions of a first example of a medical data processing apparatus.

FIG. 10 shows a medical data processing apparatus 100A according to a present embodiment. The medical data processing apparatus 100A includes processing circuitry 101, a memory 102, an input interface 103, a display 104, and a network interface 105.

The processing circuitry 101 has the same configuration as the processing circuitry 18 shown in FIG. 1, so the explanation thereof is omitted. The memory 102 has the same configuration as the main memory 19 shown in FIG. 1, so the explanation thereof is omitted. The input interface 103 has the same configuration as the input interface 60 shown in FIG. 1, so the explanation thereof is omitted. The display 104 has the same configuration as the display 70 shown in FIG. 1, so the explanation thereof is omitted. The network interface 105 has the same configuration as the network interface 17 shown in FIG. 1, so the explanation thereof is omitted.

Further, FIG. 10 shows an examination order apparatus M and an ultrasonic diagnostic apparatus 10A which are external apparatuses of the medical data processing apparatus 100A. The examination order apparatus M is, for example, an MWM server, and is connected to an apparatus such as the ultrasonic diagnostic apparatus 10A via the network N to be able to transmit and receive data. The examination order apparatus M transmits an examination order to the ultrasonic diagnostic apparatus 10A and the medical data processing apparatus 100A. The ultrasonic diagnostic apparatus 10A is an apparatus having members other than at least the association function 184 shown in FIG. 2. The function of the associating function 184 is incorporated in the medical data processing apparatus 100A as the associating function 184A.

The medical data processing apparatus 100A can receive an examination order from the examination order apparatus M. An example of the medical data processing apparatus 100A is a modality performed procedure step (MPPS) server. The MPPS server receives an examination order from the examination order apparatus M, and also receives information indicating the implementation status of the examination from the ultrasonic diagnostic apparatus 10A. Thereby, The MPPS server can manage the implementation status of each of the examinations corresponding to the examination order.

The processing circuitry 101 implements an acquiring function 183A and an associating function 184A by reading and executing a program stored in the memory 102 or incorporated directly into the processing circuit 101. Hereinafter, a case where the functions 183A and 184A function as software will be described as an example. However, all or part of the functions 183A and 184A may be provided in the medical data processing apparatus 100A as a circuit such as an ASIC.

The acquiring function 183A has a function of acquiring the ultrasonic image data in the DICOM-format from the ultrasonic diagnostic apparatus 10A, of acquiring the evidence data in the non-DICOM format indicating evidence of a diagnostic action or a treatment action from the ultrasonic diagnostic apparatus 10A, corresponding to a confirmation item related to a diagnostic action or a treatment action on a patient, and of acquiring the patient information from the examination order apparatus M. For example, the evidence data includes at least one of optical image data and the sound data. The acquiring function 183A is an example of an acquiring unit.

The associating function 184A has a function of converting the evidence data into the DICOM format by associating the patient data acquired by the acquiring function 183A with the evidence data acquired by the acquiring function 183A, and a function of storing the ultrasonic image data acquired by the acquiring function 183A and the evidence data in the DICOM format in the memory 102. The associating function 184A is an example of an associating unit.

According to the medical data processing apparatus 100A, by managing ultrasonic image data and the evidence data in the DICOM format on a patient-by-patient basis, it is possible to centrally manage the evidence for which the confirmation item has been confirmed together with the diagnostic image. Thereby, the medical data processing apparatus 100A can associate and provide the ultrasonic image data corresponding to the patient information and the evidence data on the basis of the patient information requested from the medical data processing apparatus 100A or the external apparatus.

7. Second Example of Medical Data Processing Apparatus

The converting the evidence data from the non-DICOM format to the DICOM format and managing data in the DICOM format are also possible by a medical data processing apparatus. The second example of the medical data processing apparatus is an apparatus which does not receive the patient information included in the examination order from the examination order apparatus M, unlike the medical data processing apparatus 100A shown in FIG. 10.

Figure 11:
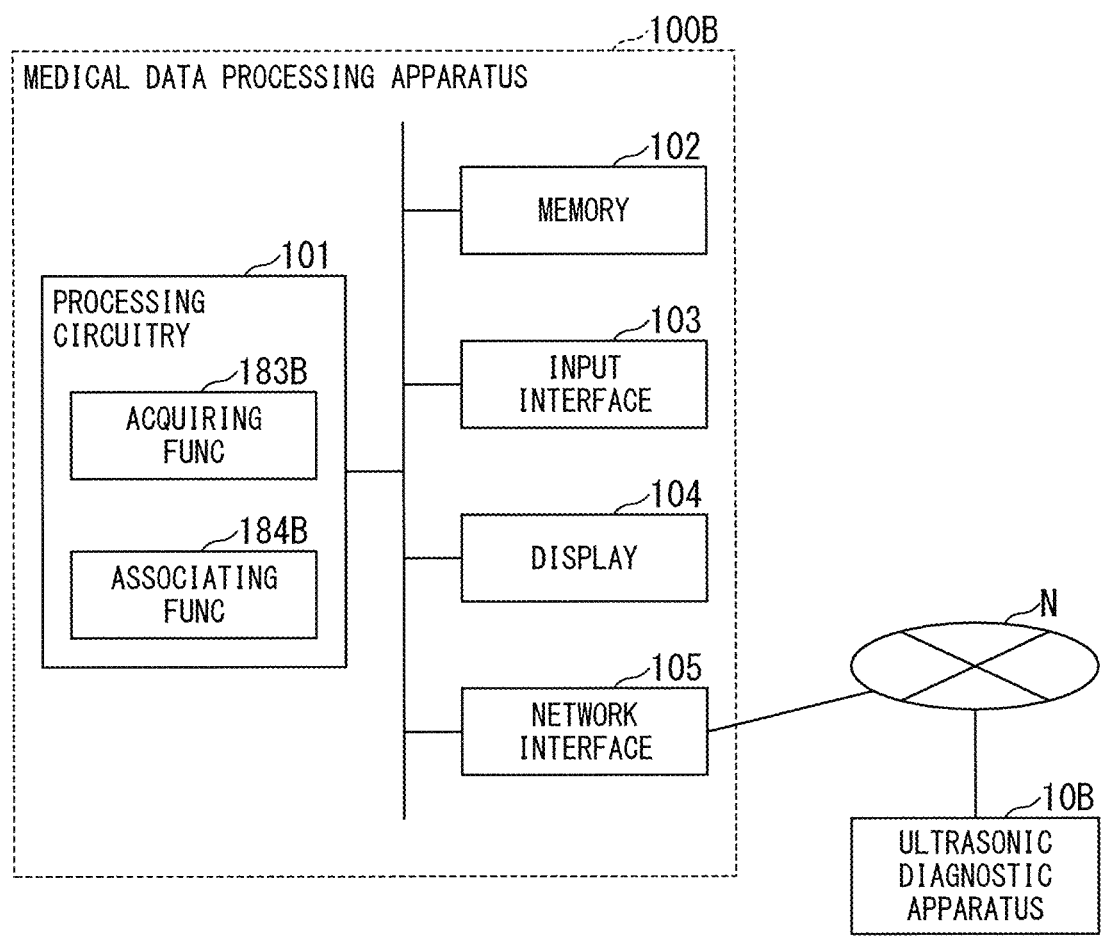
FIG. 11 is a block diagram showing a configuration and functions of a second example of the medical data processing apparatus according to the present embodiment.

FIG. 11 is a block diagram showing a configuration and functions of a second example of a medical data processing apparatus.

FIG. 11 shows a medical data processing apparatus 100B according to a present embodiment. Similar to the medical data processing apparatus 100A shown in FIG. 10, the medical data processing apparatus 100B includes the processing circuitry 101, the memory 102, the input interface 103, the display 104, and the network interface 105.

Further, FIG. 11 shows the ultrasonic diagnostic apparatus 10B which is an external apparatus of the medical data processing apparatus 100B. The ultrasonic diagnostic apparatus 10B is an apparatus having members other than at least the associating function 184 shown in FIG. 2. The function of the associating function 184 is incorporated in the medical data processing apparatus 100B as the associating function 184B.

The processing circuitry 101 implements an acquiring function 183B and an associating function 184B by reading and executing a program stored in the memory 102 or incorporated directly into the processing circuit 101. Hereinafter, the case where the functions 183B and 184B function as software will be described as an example. However, all or part of the functions 183B and 184B may be provided in the medical data processing apparatus 100B as a circuit such as an ASIC.

The acquiring function 183B has a function of acquiring a set of the ultrasonic image data in the DICOM format and the evidence data in the non-DICOM format indicating evidence of a diagnostic action or a treatment action corresponding to a confirmation item related to the diagnostic action or the treatment action on the patient. For example, the evidence data includes at least one of the optical image data and the sound data. The acquiring function 183B is an example of an acquiring unit.

The associating function 184B has a function of converting the evidence data into the DICOM format by associating the set of evidence data acquired by the acquiring function 183B with the patient information included as the tag data in the ultrasonic image data of the set, and of storing the set of ultrasonic image data and the evidence data in the DICOM format in the memory 102. The associating function 184B is an example of an associating unit.

According to the medical data processing apparatus 100B, by managing ultrasonic image data and the evidence data in the DICOM format on a patient-by-patient basis, it is possible to centrally manage the evidence for which the confirmation item has been confirmed together with the diagnostic image. Thereby, the medical data processing apparatus 100B can associate and provide the ultrasonic image data corresponding to the patient information and the evidence data on the basis of the patient information requested from the medical data processing apparatus 100B or the external apparatus.

According to at least one of the embodiments described above, it is possible to improve the diagnostic efficiency of the patient.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
processing circuitry configured to
instruct an acquisition of at least one of optical image data and sound data by means of a sound instruction, the sound instruction corresponding to a confirmation item related to a diagnostic action or treatment action on a patient and being determined for each disorder name or examination type,
acquire at least one of the optical image data and the sound data as evidence data corresponding to the sound instruction,
associate ultrasonic image data acquired by an ultrasonic scan with the acquired evidence data, and
store the association in a memory.

2. The ultrasonic diagnostic apparatus according to claim 1, further comprising:
an optical camera configured to acquire the optical image data.

3. The ultrasonic diagnostic apparatus according to claim 1, further comprising:
a microphone configured to detect sound and acquire the sound data.

4. The ultrasonic diagnostic apparatus according to claim 1, wherein the processing circuitry is further configured to generate the ultrasonic image data by controlling an ultrasonic probe to execute the ultrasonic scan.

5. The ultrasonic diagnostic apparatus according to claim 1, wherein
the ultrasonic diagnostic apparatus is a portable apparatus.

6. The ultrasonic diagnostic apparatus according to claim 1, wherein the processing circuitry is further configured to control an output of particular sound data for instructing acquisition of the evidence data related to the confirmation item.

7. The ultrasonic diagnostic apparatus according to claim 6, wherein the processing circuitry is further configured to output, when the examination type is a stress echo examination, the particular sound data for instructing the acquisition of the evidence data related to the confirmation item on and after the stress.

8. The ultrasonic diagnostic apparatus according to claim 1, wherein the processing circuitry is further configured to
generate, when associating the ultrasonic image data acquired by the ultrasonic scan with the evidence data related to the confirmation item, associated data in which the ultrasonic image data and the evidence data related to the confirmation item are directly associated, and
store the associated data in the memory.

9. The ultrasonic diagnostic apparatus according to claim 8, wherein the processing circuitry is further configured to
transmit the associated data to an external apparatus and receive particular sound data for instructing acquisition of the evidence data related to the confirmation item, the particular sound data corresponding to the associated data from the external apparatus, and
control an output of the particular sound data.

10. The ultrasonic diagnostic apparatus according to claim 1, wherein the processing circuitry is further configured to
convert the evidence data related to the confirmation item from non-DICOM (Digital Imaging and Communications in Medicine) to a DICOM format, and
store the ultrasonic image data and the evidence data related to the confirmation item both in the DICOM format in the memory.

11. The ultrasonic diagnostic apparatus according to claim 10, wherein the processing circuitry is further configured to attach subject information corresponding to an ultrasonic examination to the evidence data related to the confirmation item acquired during the ultrasonic examination.

12. The ultrasonic diagnostic apparatus according to claim 1, wherein the processing circuitry is further configured to
acquire at least two pieces among a plurality of pieces of the optical image data and a plurality of pieces of the sound data according to the instruction of the acquisition, and
associate, when all of the at least two pieces on a same patient have been acquired, the ultrasonic image data with the all the acquired at least two pieces.

13. An ultrasonic diagnostic apparatus, comprising:
processing circuitry configured to
instruct, via an instruction, an acquisition of at least one of optical image data and sound data,
acquire at least one of the optical image data and the sound data as evidence data corresponding to the instruction
associate ultrasonic image data acquired by the ultrasonic scan with the acquired evidence data, and
store the association in a memory, and
an optical camera configured to acquire dynamic image data as the optical image data, wherein the processing circuitry is further configured to
output, when an examination type for an ultrasonic scan is an examination in an emergency mode, a particular sound data for instructing the acquisition of the dynamic image data as data related to a confirmation item before an ultrasonic examination, and
control the optical camera to acquire the dynamic image data.

14. An ultrasonic diagnostic apparatus, comprising:
processing circuitry configured to
instruct, via an instruction, an acquisition of at least one of optical image data and sound data,
acquire at least one of the optical image data and the sound data as evidence data corresponding to the instruction
associate ultrasonic image data acquired by the ultrasonic scan with the acquired evidence data, and
store the association in a memory, wherein the processing circuitry is further configured to determine whether or not all of the evidence data on a same patient have been acquired in response to an input from a user via an input interface.

* * * * *